United States Patent
Sugawara et al.

(10) Patent No.: US 11,219,688 B2
(45) Date of Patent: Jan. 11, 2022

(54) ABSORPTION PROMOTER AND USE FOR SAME

(71) Applicant: Moresco Corporation, Kobe (JP)

(72) Inventors: Mitsuru Sugawara, Hokkaido (JP); Yuki Sato, Hokkaido (JP); Yoh Takekuma, Hokkaido (JP); Shingo Maruyama, Hyogo (JP)

(73) Assignee: MORESCO CORPORATION, Hyogo (JP)

( * ) Notice: Subject to any disclaimer, the term of this patent is extended or adjusted under 35 U.S.C. 154(b) by 85 days.

(21) Appl. No.: 16/489,181

(22) PCT Filed: Mar. 2, 2018

(86) PCT No.: PCT/JP2018/008081
§ 371 (c)(1),
(2) Date: Aug. 27, 2019

(87) PCT Pub. No.: WO2018/159826
PCT Pub. Date: Sep. 7, 2018

(65) Prior Publication Data
US 2019/0374645 A1 Dec. 12, 2019

(30) Foreign Application Priority Data
Mar. 3, 2017 (JP) .............................. JP2017-040896

(51) Int. Cl.
| A61K 47/12 | (2006.01) |
| A61K 9/107 | (2006.01) |
| A61K 31/121 | (2006.01) |
| A61K 31/122 | (2006.01) |
| A61K 47/44 | (2017.01) |

(52) U.S. Cl.
CPC .............. A61K 47/12 (2013.01); A61K 9/107 (2013.01); A61K 31/121 (2013.01); A61K 31/122 (2013.01); A61K 47/44 (2013.01)

(58) Field of Classification Search
None
See application file for complete search history.

(56) References Cited

U.S. PATENT DOCUMENTS

| 4,442,090 A | 4/1984 | Kakeya et al. | |
| 6,004,578 A * | 12/1999 | Lee ...................... | A61K 9/0014 424/443 |
| 6,251,369 B1 * | 6/2001 | Stoltz ..................... | A61K 8/046 424/45 |
| 2004/0013697 A1 | 1/2004 | Berndl et al. | |
| 2004/0067202 A1 | 4/2004 | Looker et al. | |
| 2011/0123652 A1 | 5/2011 | Berndl et al. | |
| 2012/0225953 A1 | 9/2012 | Berndl et al. | |
| 2014/0135388 A1 | 5/2014 | Berndl et al. | |
| 2019/0106373 A1 | 4/2019 | Maruyama | |

FOREIGN PATENT DOCUMENTS

| EP | 3441382 A1 | 2/2019 |
| GB | 1165199 A | 9/1969 |
| JP | 57-080315 A | 5/1982 |
| JP | 2001-502693 A | 2/2001 |
| JP | 2003-534369 A | 11/2003 |
| JP | 201047541 A | 3/2010 |
| WO | 199817315 A2 | 4/1998 |
| WO | 2012/051727 A2 | 4/2012 |
| WO | 2017175522 A1 | 10/2017 |

OTHER PUBLICATIONS

STN Accession No. 2001:464261 (Year: 2001).*
International Preliminary Report on Patentability for PCT Application No. PCT/JP2018/008081 dated Sep. 3, 2019.
International Search Report from PCT Application No. PCT/JP2018/008081 dated Jun. 5, 2018.
Office Action from Japanese Application No. 2019-503151 dated Jun. 30, 2020.
Extended European Search Report from corresponding European Application No. 18761919.2 dated Dec. 22, 2020.

* cited by examiner

*Primary Examiner* — Craig D Ricci
(74) *Attorney, Agent, or Firm* — Harness Dickey & Pierce P.L.C.

(57) ABSTRACT

To provide an absorption promotor that is capable of improving the efficiency in absorption of a pharmaceutical drug and that is highly stable, an absorption promotor includes an oxa acid having a structure represented by the formula (1) below,

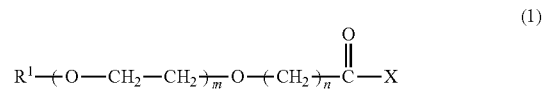

where $R^1$ represents a linear or branched hydrocarbon group having 1 to 40 carbon atoms, one or more but not all carbon atoms of which hydrocarbon group have optionally been substituted by an oxygen atom, a nitrogen atom, or a sulfur atom, the hydrocarbon group being saturated or unsaturated; m represents a real number of 0 to 50; n represents an integer of 1 to 5; and —C(=O)—X represents a functional group capable of chemical reaction.

7 Claims, 8 Drawing Sheets

ABSORPTION PROMOTER AND USE FOR SAME

PRIORITY STATEMENT

Figure 1:
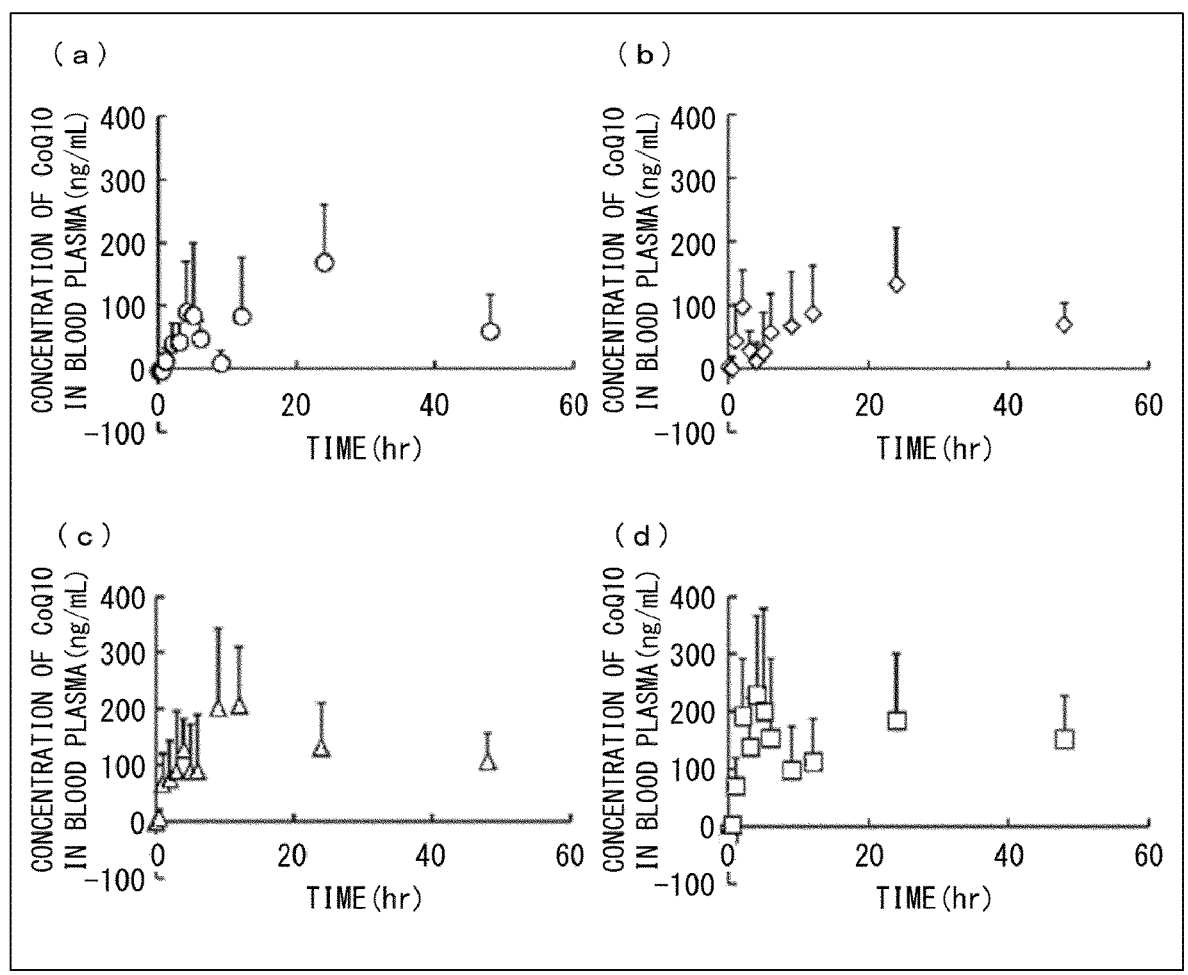

This application is a national stage application under 35 U.S.C. § 371 of PCT International Application No. PCT/JP2018/008081, which has an international filing date of Mar. 2, 2018 and claims priority under 35 U.S.C. § 119 to JP 2017-040896 filed on Mar. 3, 2017. The contents of each application recited above are incorporated herein by reference in their entirety.

TECHNICAL FIELD

The present invention relates to an absorption promotor and use thereof. The present invention more particularly relates to (i) an absorption promotor, (ii) an absorption promotor composition including an absorption promotor, (iii) an absorption promotor kit including an absorption promotor, and (iv) a pharmaceutical composition including an absorption promotor.

BACKGROUND ART

A pharmaceutical drug having a low absorption efficiency (gastrointestinal absorption) after oral administration involves a large individual difference in terms of the amount of pharmaceutical drug absorbed by the body, with the result of a difference in drug efficacy. To formulate such a pharmaceutical drug as a pharmaceutical agent, it is important to impart a stable, high absorption efficiency to the pharmaceutical drug. Many compounds as development candidates in recent years have extremely low solubility and belong to Class 4 of the BSC classification.

The BSC (biopharmaceutics classification system) classification is a concept proposed as a pharmaceutical drug classification based on the combination of (i) the degree of water solubility and (ii) the degree of digestive tract membrane permeability. A pharmaceutical drug that belongs to Class 4 of the BSC classification characteristically has low water solubility and low membrane permeability. A pharmaceutical drug that belongs to Class 4 of the BSC classification thus has low gastrointestinal absorption and is difficult to formulate.

The gastrointestinal absorption of a pharmaceutical drug can be improved by, for example, emulsifying the pharmaceutical drug. Some pharmaceutical drugs that belong to Class 4 of the BSC classification have been proven to have improved gastrointestinal absorption by emulsification. Examples of the emulsion include water, oil, and a surfactant such as an emulsifier as well as an auxiliary surfactant and a solubilizing agent as necessary. Research is being conducted on a new emulsifying measure.

Patent Literature 1, for example, discloses a self-emulsifiable composition based on (i) an active substance component and (ii) a formulation base including a lipid component and a binder component.

CITATION LIST

Patent Literature

[Patent Literature 1]
Japanese Translation of PCT International Application, Tokuhyo, No. 2003-534369 (Publication Date: Nov. 18, 2003)

SUMMARY OF INVENTION

Technical Problem

The self-emulsifiable composition disclosed in Patent Literature 1 unfortunately leaves room for improvement in terms of the efficiency in absorption of a pharmaceutical drug and stability.

Patent Literature 1 also discloses that using an emulsifier such as Cremophor (registered trademark) or Tween (registered trademark) at a high dose may cause local and/or systemic toxicity to be manifested. In addition, Patent Literature 1 discloses that an emulsifying phospholipid, in particular lecithin, is not stable.

An aspect of the present invention has been accomplished in view of the above issues. It is an object of an aspect of the present invention to provide an absorption promotor that is capable of improving the efficiency in absorption of a pharmaceutical drug, in particular a poorly absorbable pharmaceutical drug, and that is highly stable.

Solution to Problem

The inventors of the present invention conducted diligent research to attain the above object, and thereby discovered that use of an oxa acid having a particular structure makes it possible to provide an absorption promotor that is capable of improving the efficiency in absorption of a pharmaceutical drug, in particular a poorly absorbable pharmaceutical drug, and that is highly stable. The inventors have thus completed the present invention. Specifically, an embodiment of the present invention is arranged as follows:

[1] An absorption promotor, including: an oxa acid having a structure represented by formula (1) below,

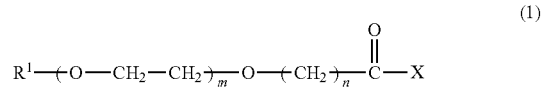

(1)

where $R^1$ represents a linear or branched hydrocarbon group having 1 to 40 carbon atoms, one or more but not all carbon atoms of which hydrocarbon group have optionally been substituted by an oxygen atom, a nitrogen atom, or a sulfur atom, the hydrocarbon group being saturated or unsaturated; m represents a real number of 0 to 50; n represents an integer of 1 to 5; and —C(=O)—X represents a functional group capable of chemical reaction.

[2] The absorption promotor according to [1], wherein in the formula (1), $R^1$ is a linear or branched hydrocarbon group having 14 to 40 carbon atoms.

[3] An absorption promotor composition, including: an absorption promotor according to [1] or [2]; and oil.

[4] The absorption promotor composition according to [3], further including: water.

[5] The absorption promotor composition according to [3] or [4], further including: a surfactant.

[6] The absorption promotor composition according to any one of [3] to [5], wherein the absorption promotor, together with the oil, forms micelles; and the micelles have an average particle diameter of not more than 1000 nm.

[7] The absorption promotor composition according to [6], wherein not less than 5% of the micelles each have a particle diameter of not more than 100 nm.

[8] The absorption promotor composition according to any one of [4] to [7], wherein the absorption promotor is contained in an amount of 5% by weight to 20% by weight; the oil is contained in an amount of 5% by weight to 30% by weight; and the water is contained in an amount of 50% by weight to 90% by weight.

[9] An absorption promotor kit, including: an absorption promotor according to [1] or [2]; and oil.

[10] A pharmaceutical composition, including: an absorption promotor according to [1] or [2] or an absorption promotor composition according to any one of [3] to [8]; and a pharmaceutical drug.

Advantageous Effects of Invention

An aspect of the present invention advantageously provides an absorption promotor that is capable of improving the efficiency in absorption of a pharmaceutical drug, in particular a poorly absorbable pharmaceutical drug, and that is highly stable.

An aspect of the present invention advantageously provides an absorption promotor composition that is capable of improving the efficiency in absorption of a pharmaceutical drug, in particular a poorly absorbable pharmaceutical drug, and that is highly stable.

An aspect of the present invention advantageously provides an absorption promotor kit that is capable of improving the efficiency in absorption of a pharmaceutical drug, in particular a poorly absorbable pharmaceutical drug, and that is highly stable.

BRIEF DESCRIPTION OF DRAWINGS (a) of FIG. 1 is a graph that shows how the concentration of CoQ10 in blood plasma changed in Example 7 (which involved use of the absorption promotor composition of Example 1). (b) of FIG. 1 is a graph that shows how the concentration of CoQ10 in blood plasma changed in Example 8 (which involved use of the absorption promotor composition of Example 2). (c) of FIG. 1 is a graph that shows how the concentration of CoQ10 in blood plasma changed in Example 9 (which involved use of the absorption promotor composition of Example 3). (d) of FIG. 1 is a graph that shows how the concentration of CoQ10 in blood plasma changed in Example (which involved use of the absorption promotor composition of Example 4).

Figure 2:
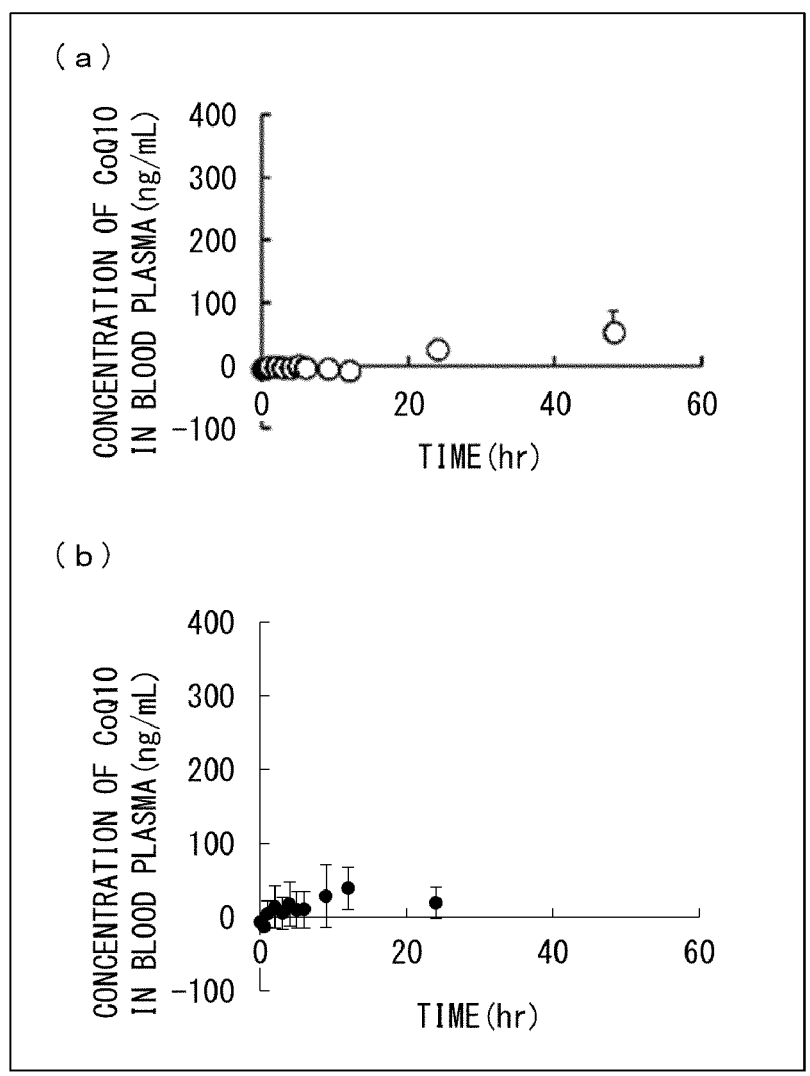

(a) of FIG. 2 is a graph that shows how the concentration of CoQ10 in blood plasma changed in Comparative Example 2 (which involved administration of CoQ10 only). (b) of FIG. 2 is a graph that shows how the concentration of CoQ10 in blood plasma changed in Comparative Example 1 (which involved use of sodium taurocholate and phosphatidylcholine as emulsifiers).

Figure 3:
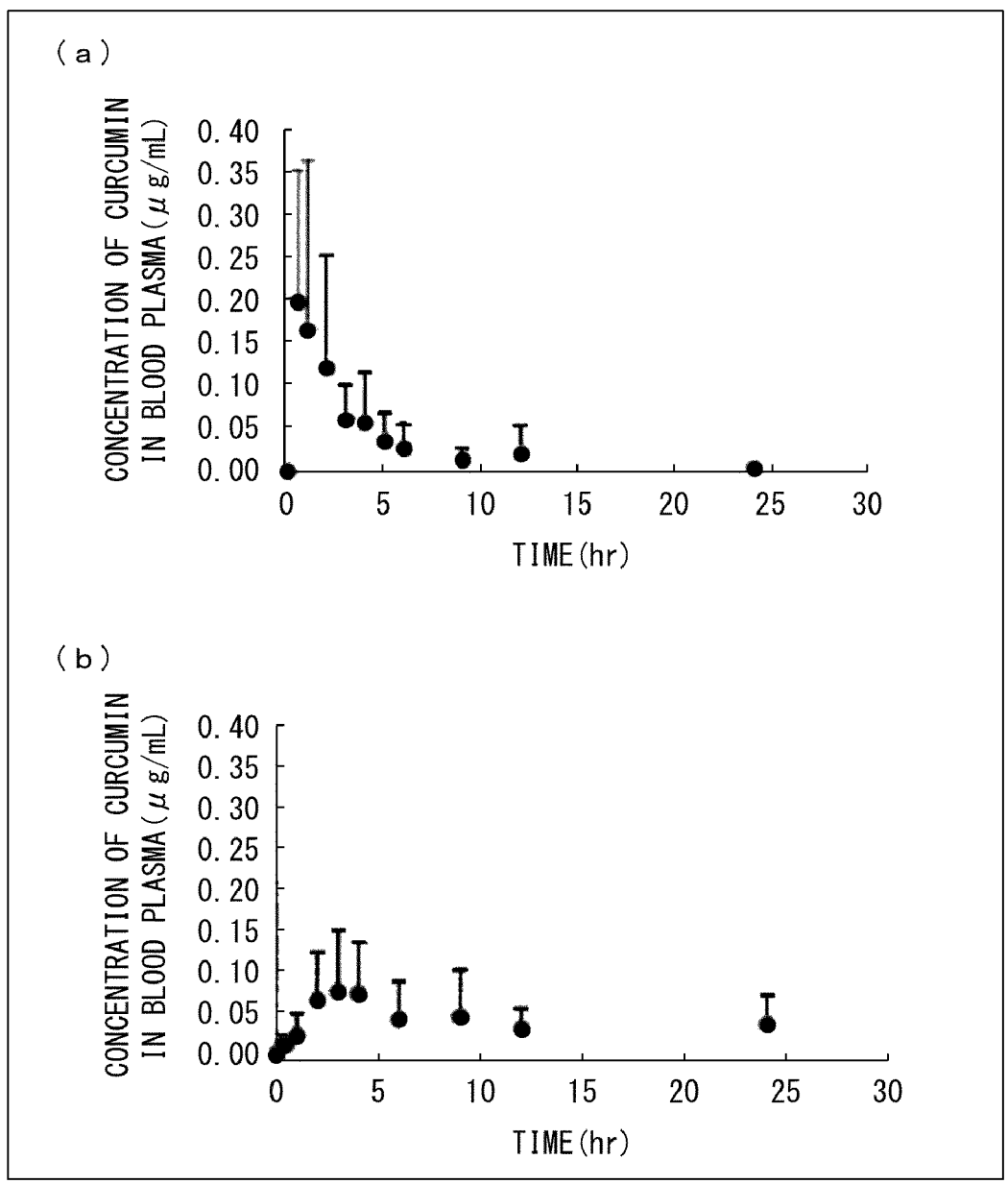

(a) of FIG. 3 is a graph that shows how the concentration of curcumin in blood plasma changed in Example 11. (b) of FIG. 3 is a graph that shows how the concentration of curcumin in blood plasma changed in comparative Example 3.

Figure 4:
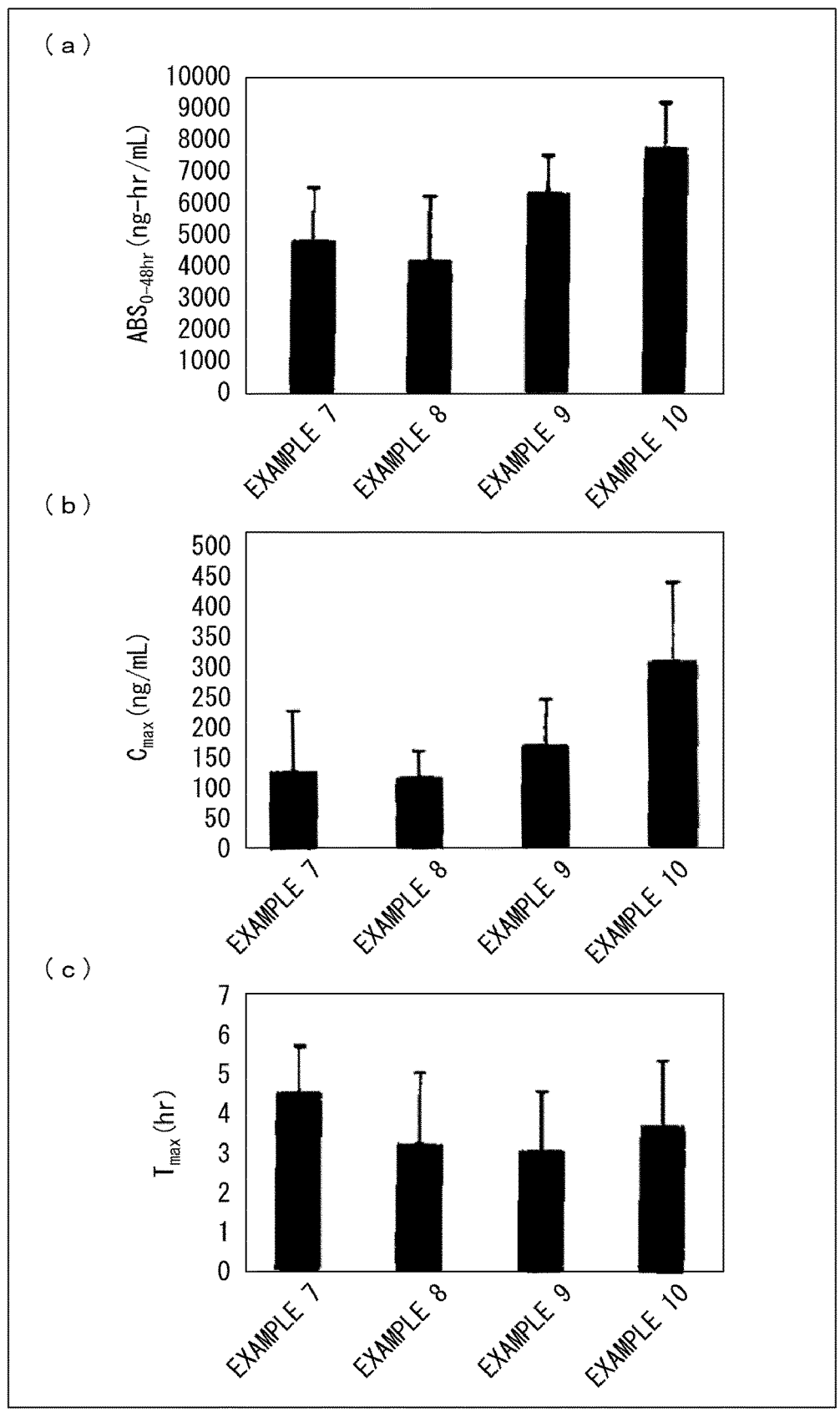

(a) of FIG. 4 is a graph that compares $ABS_{0-48hr}$ values about how the concentration of CoQ10 in blood plasma changed in Examples 7 to 10, which involved use of the respective absorption promotor compositions of Examples 1 to 4. (b) of FIG. 4 is a graph that compares $C_{max}$ values about how the concentration of CoQ10 in blood plasma changed in Examples 7 to 10, which involved use of the respective absorption promotor compositions of Examples 1 to 4. (c) of FIG. 4 is a graph that compares $T_{max}$ values about how the concentration of CoQ10 in blood plasma changed in Examples 7 to 10, which involved use of the respective absorption promotor compositions of Examples 1 to 4.

Figure 5:
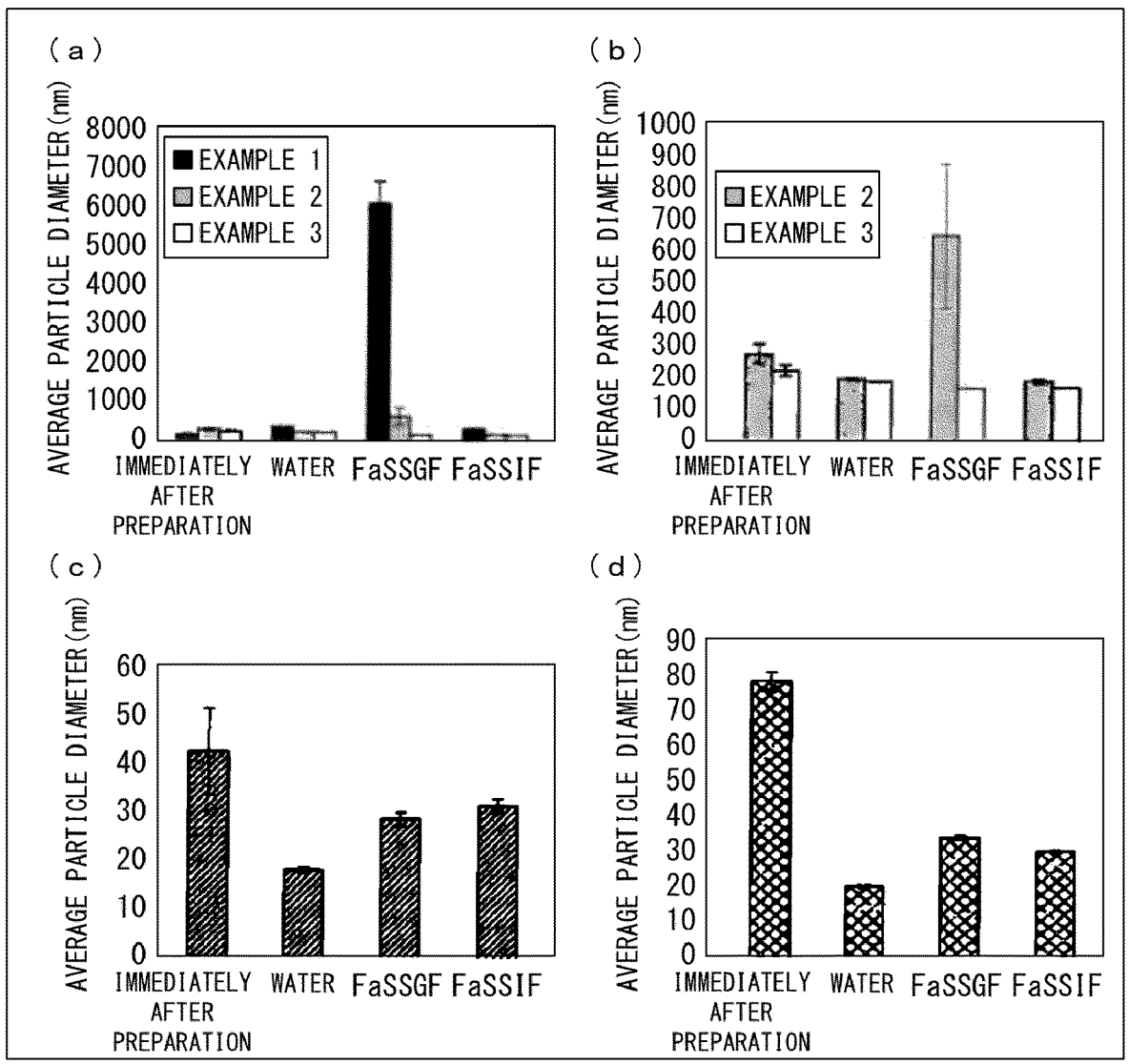

(a) of FIG. 5 is a graph that shows the average particle diameter of micelles in each of the respective absorption promotor compositions of Examples 1 to 3 for cases where each of the absorption promotor compositions was incubated with use of water, a FaSSGF, or a FaSSIF. (b) of FIG. 5 is a graph that shows the average particle diameter of micelles in each of the respective absorption promotor compositions of Examples 2 and 3 for cases where each of the absorption promotor compositions was incubated with use of water, a FaSSGF, or a FaSSIF. (c) of FIG. 5 is a graph that shows the average particle diameter of micelles in the absorption promotor composition of Example 4 for cases where the absorption promotor composition was incubated with use of water, a FaSSGF, or a FaSSIF. (d) of FIG. 5 is a graph that shows the average particle diameter of micelles in the absorption promotor composition of Example 6 for cases where the absorption promotor composition was incubated with use of water, a FaSSGF, or a FaSSIF.

Figure 6:
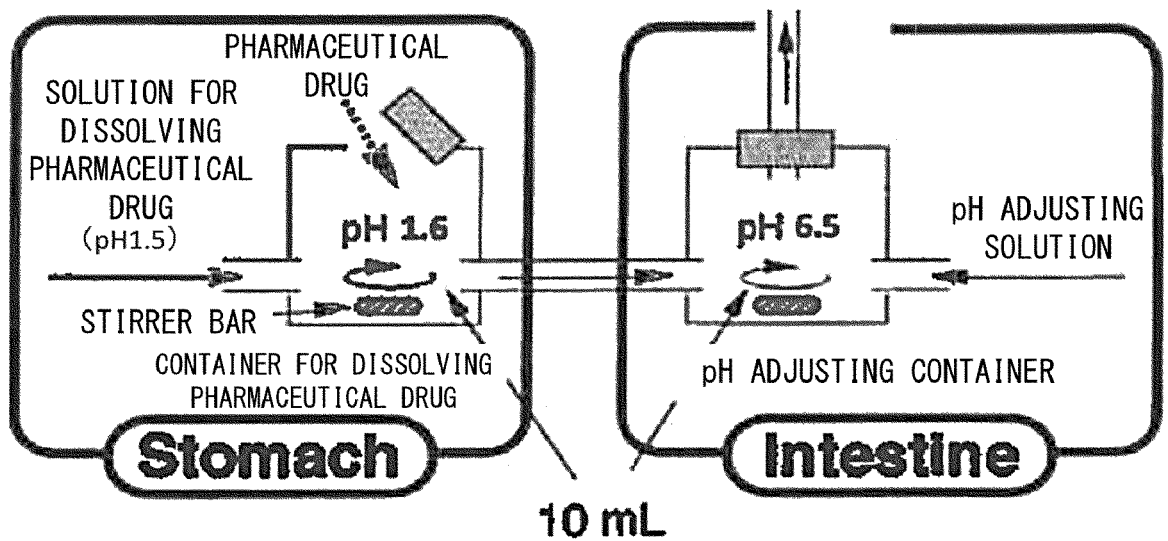

FIG. 6 is a conceptual diagram of an absorption predicting system used as a model that simulates an environment in a living body for Examples of the present invention.

Figure 7:
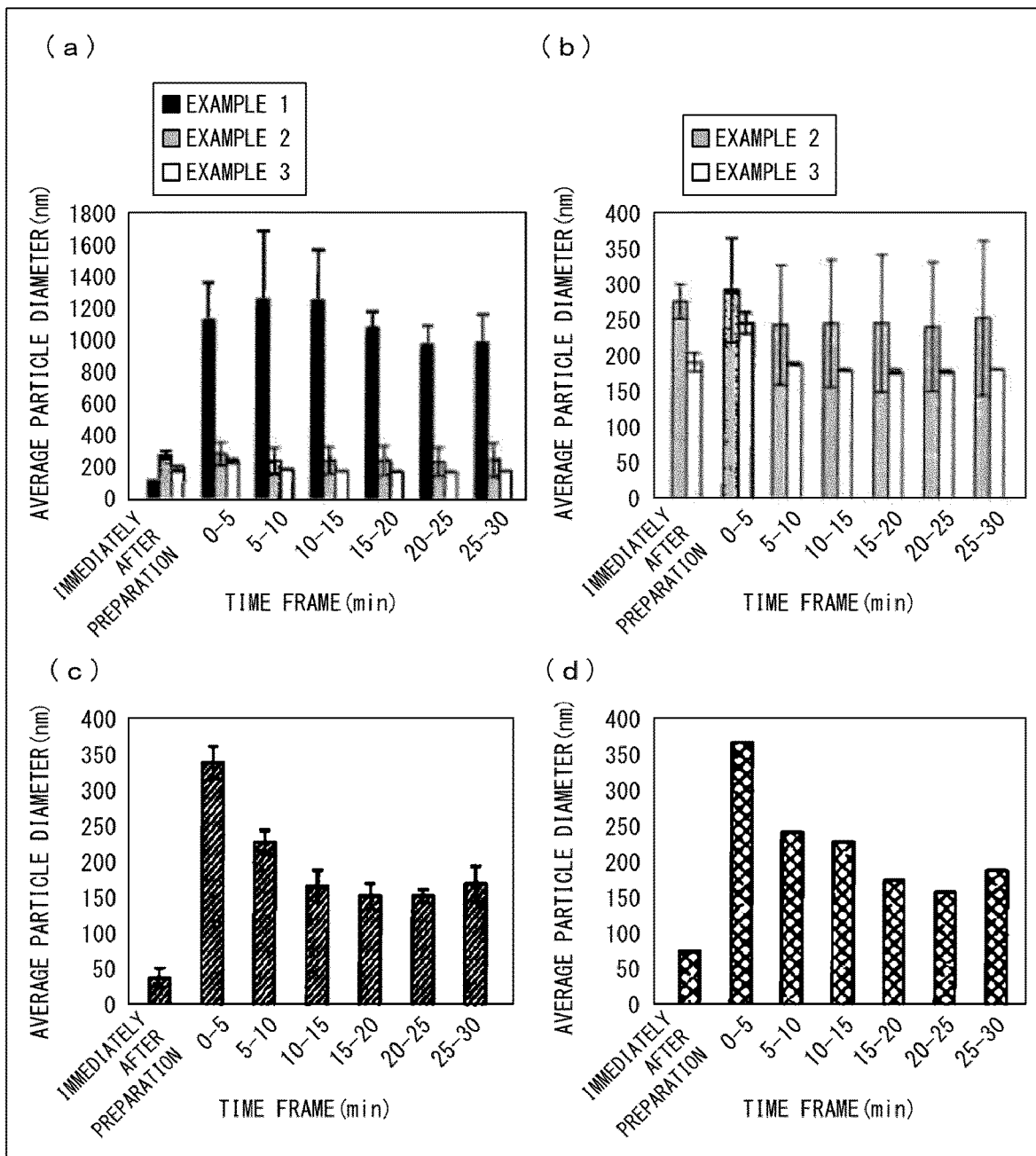

(a) of FIG. 7 is a graph that shows the average particle diameter, during each time frame, of micelles in each of the respective absorption promotor compositions of Examples 1 to 3 that has passed through a FaSSGF and a FaSSIF. (b) of FIG. 7 is a graph that shows the average particle diameter, during each time frame, of micelles in each of the respective absorption promotor compositions of Examples 2 and 3 that has passed through a FaSSGF and a FaSSIF. (c) of FIG. 7 is a graph that shows the average particle diameter, during each time frame, of micelles in the absorption promotor composition of Example 4 that has passed through a FaSSGF and a FaSSIF. (d) of FIG. 7 is a graph that shows the average particle diameter, during each time frame, of micelles in each of the absorption promotor composition of Example 6 that has passed through a FaSSGF and a FaSSIF.

Figure 8:
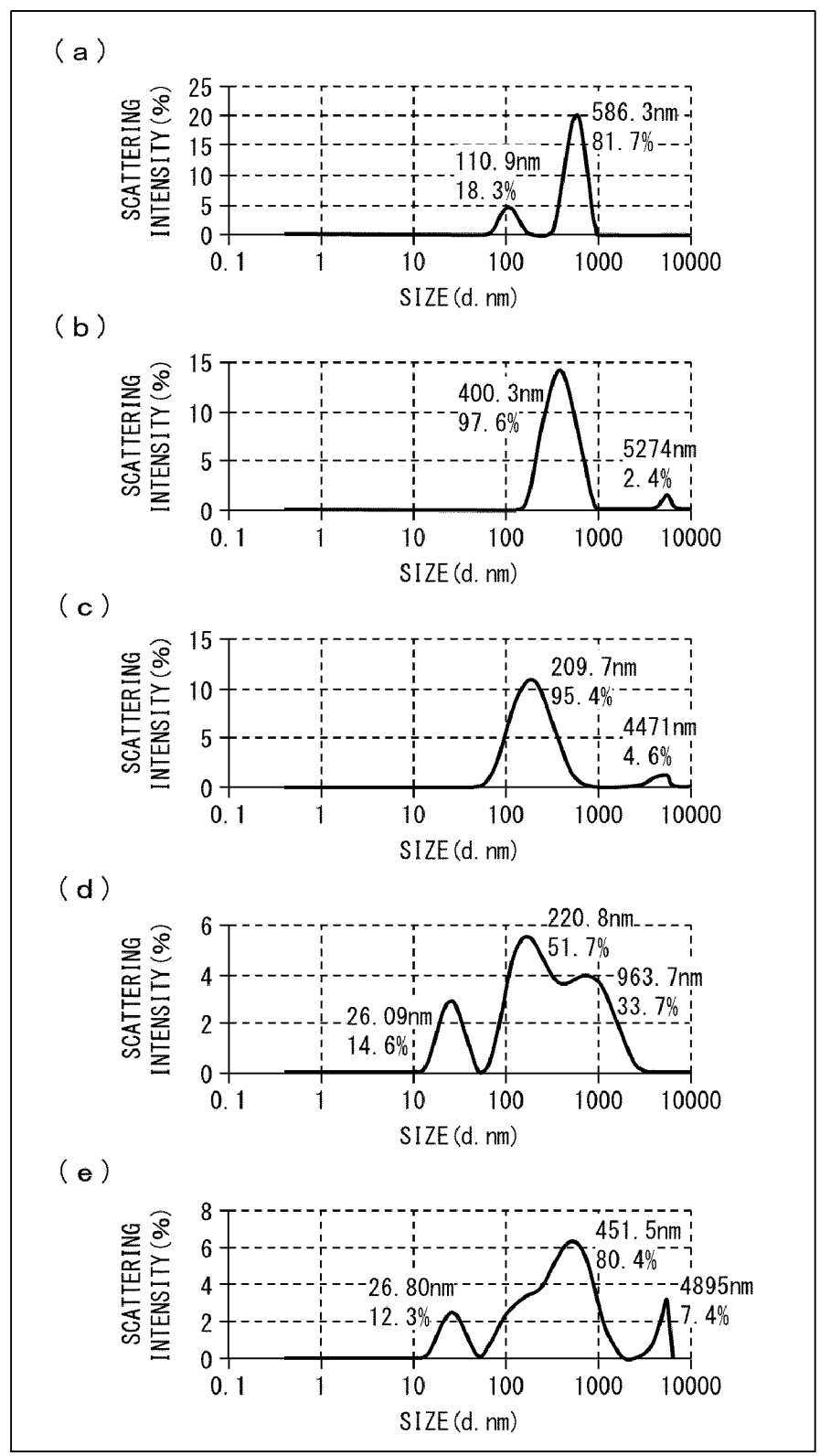

(a) of FIG. 8 is a graph that shows the particle size distribution of micelles in the absorption promotor composition of Example 1 that has passed through a FaSSGF and a FaSSIF. (b) of FIG. 8 is a graph that shows the particle size distribution of micelles in the absorption promotor composition of Example 2 that has passed through a FaSSGF and a FaSSIF. (c) of FIG. 8 is a graph that shows the particle size distribution of micelles in the absorption promotor composition of Example 3 that has passed through a FaSSGF and a FaSSIF. (d) of FIG. 8 is a graph that shows the particle size distribution of micelles in the absorption promotor composition of Example 4 that has passed through a FaSSGF and a FaSSIF. (e) of FIG. 8 is a graph that shows the particle size distribution of micelles in the absorption promotor composition of Example 6 that has passed through a FaSSGF and a FaSSIF.

DESCRIPTION OF EMBODIMENTS

The following will describe an embodiment of the present invention in detail. Note, however, that the present invention is not limited to that embodiment. The present invention can be carried out in specific forms into which various modifications are incorporated within the scope set forth herein. All of the academic documents and patent literatures listed herein are incorporated by reference herein. Unless otherwise specified herein, "A to B" which indicates a numerical range means "not less than A and not more than B".

[1. Absorption Promotor]

An absorption promotor in accordance with an embodiment of the present invention includes an oxa acid having a particular structure.

The absorption promotor, which includes the oxa acid, is capable of emulsifying a pharmaceutical drug. The absorption promotor is not separated and is stable during preparation of an absorption promotor composition described later. Further, the absorption promotor composition includes micelles having a small average particle diameter. This makes it possible to improve the efficiency in absorption of a pharmaceutical drug, in particular a poorly absorbable pharmaceutical drug, after oral administration.

The oxa acid has a structure represented by the formula (1) below.

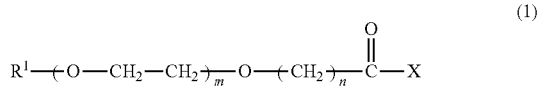

(1)

where $R^1$ represents a linear or branched hydrocarbon group having 1 to 40 carbon atoms, one or more but not all carbon atoms of which hydrocarbon group have optionally been substituted by an oxygen atom, a nitrogen atom, or a sulfur atom, the hydrocarbon group being saturated or unsaturated; m represents a real number of 0 to 50; n represents an integer of 1 to 5; and —C(=O)—X represents a functional group capable of chemical reaction.

In the formula (1) above, $R^1$ simply needs to have 1 to 40 carbon atoms, but preferably has 2 to 40 carbon atoms, more preferably 4 to 40 carbon atoms, even more preferably 6 to 40 carbon atoms, even more preferably 8 to 40 carbon atoms, particularly preferably 14 to 40 carbon atoms, most preferably 18 to 40 carbon atoms. Further, $R^1$ may be linear or branched.

$R^1$ may be a hydrocarbon group, or may be a hydrocarbon group one or more but not all carbon atoms of which hydrocarbon group may have been substituted by an oxygen atom, a nitrogen atom, or a sulphur atom.

$R^1$ may be saturated or unsaturated. In other words, $R^1$ may have a carbon-carbon double bond, a carbon-carbon triple bond, or a combination thereof. In particular, in a case where $R^1$ is an unsaturated hydrocarbon group, $R^1$ more preferably contains a carbon-carbon double bond. In a case where $R^1$ is an unsaturated hydrocarbon group, $R^1$ may contain any number of carbon-carbon double bonds, carbon-carbon triple bonds, or combinations thereof. The total number is, for example, 1 to 5, preferably 1 to 3.

m simply needs to be a real number of 0 to 50. m is preferably a real number of 1 to 50, more preferably a real number of 4 to 45, even more preferably a real number of 8 to 40. m is preferably within the above range, as that makes it possible to produce an absorption promotor that is not separated and is stable during preparation.

n simply needs to be an integer of 1 to 5. n may alternatively be an integer of 1 to 4 or an integer of 1 to 3.

In the formula (1) above, —C(=O)—X simply needs to be a functional group capable of chemical reaction. Specifically, —C(=O)—X simply needs to be a group capable of chemical reaction with a molecule present in the living body, the group being, for example, (i) an active ester group such as N-hydroxysuccinimido ester or (ii) a group (such as a maleimide group). In a case where —C(=O)—X is a group capable of chemical reaction, an absorption promotor having a structure represented by the formula (1) above reacts with a molecule present in the living body. This improves the efficiency in absorption of a pharmaceutical drug. The absorption promotor is thus suitably usable as a promotor of absorption of a pharmaceutical drug.

More specifically, the active ester group is, for example, (i) an active ester in which X represents a succinimidyloxy group, a 4-nitrophenoxy group, a phthalimidyloxy group, a 1-imidazolyl group, a pentafluorophenoxy group, a benzotriazole-1-yloxy group, or a 7-azabenzotriazole-1-yloxy group or (ii) maleimide ester.

X in the formula (1) above is, in particular, preferably a group represented by the following formula (a) or (b):

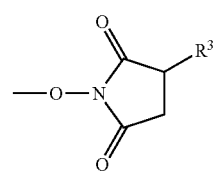

(a)

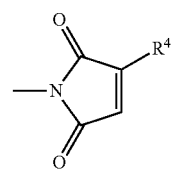

(b)

In the formula (a), $R^3$ represents a hydrogen atom or a sulfo group. The sulfo group is, for example, sodium sulphonate or potassium sulphonate. $R^3$ is preferably a hydrogen atom. In the formula (b), $R^4$ is a hydrogen atom or a linear or branched hydrocarbon group having 1 to 5 carbon atoms.

The oxa acid has an HLB value of preferably 2 to 15, more preferably 2 to 9.

The absorption promotor includes various oxa acids having respective hydrophile-lipophile balances different from each other. The absorption promotor is suitably usable for polarity control in dosage form design of a pharmaceutical drug, in particular a poorly absorbable pharmaceutical drug.

The HLB value is an HLB value calculated by Davis method. Davis method refers to a method of calculating an HLB value by dividing a molecule into groups (atomic groups) and using HLB group numbers given to various groups and unique to the respective groups. Specifically, in Davis method, the HLB value is calculated on the basis of "The hydrophilic-lipophilic balance(HLB) of the emulsifier" at pages 429 to 431 of "Gas/Liquid and Liquid/Liquid Interfaces. Proceedings of 2nd International Congress Surface Activity, Butterworths, London 1957".

The oxa acid may be any oxa acid represented by the formula (1) above. Specific examples of the oxa acid include an oxa acid having a structure represented by the following formula (2):

(2)

In the formula (2), $R^2$ represents a linear or branched hydrocarbon group having 1 to 40 carbon atoms, one or more but not all carbon atoms of which hydrocarbon group have optionally been substituted by an oxygen atom, a nitrogen atom, or a sulfur atom, the hydrocarbon group being saturated or unsaturated; x represents a real number of 0 to 50; and y represents an integer of 1 to 5.

In the formula (2) above, $R^2$ simply needs to have 1 to 40 carbon atoms, but preferably has 2 to 40 carbon atoms, more preferably 4 to 40 carbon atoms, even more preferably 6 to 40 carbon atoms, even more preferably 8 to 40 carbon atoms, particularly preferably 14 to 40 carbon atoms, most preferably 18 to 40 carbon atoms. Further, $R^2$ may be linear or branched. The number of carbon atoms of $R^2$ being within the above range makes it possible to produce an absorption promotor composition that is not separated and is stable during preparation and that has micelles having a small average particle diameter.

$R^2$ may be a hydrocarbon group, or may be a hydrocarbon group one or more but not all carbon atoms of which hydrocarbon group may have been substituted by an oxygen atom, a nitrogen atom, or a sulphur atom.

$R^2$ may be saturated or unsaturated. In other words, $R^2$ may have a carbon-carbon double bond, a carbon-carbon triple bond, or a combination thereof. In particular, in a case where $R^2$ is an unsaturated hydrocarbon group, $R^2$ more preferably contains a carbon-carbon double bond. The number of carbon-carbon double bonds, carbon-carbon triple bonds, or combinations thereof in $R^2$ is as described above for $R^1$.

In a case where $R^2$ is, for example, a linear or branched alkyl group, alkenyl group, or alkadienyl group having 1 to 40 carbon atoms, $R^2$ is, for example, methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, stearyl group (oxtadecyl group), nonadecyl group, icosyl group, henicosyl group, docosyl group, tricosyl group, tetracosyl group, pentacosyl group, hexacosyl group, heptacosyl group, octacosyl group, nonacosyl group, triacontyl group, hentriacontyl group, dotriacontyl group, tritriacontyl group, tetratriacontyl group, pentatriacontyl group, hexatriacontyl group, heptatriacontyl group, octatriacontyl group, nonatriacontyl group, tetracontyl group, ethenyl group, propenyl group, butenyl group, pentenyl group, hexenyl group, heptenyl group, octenyl group, nonenyl group, decenyl group, dodecenyl group, undecenyl group, tridecenyl group, tetradecenyl group, pentadecenyl group, hexadecenyl group, heptadecenyl group, octadecenyl group, nonadecenyl group, icosenyl group, henicosenyl group, docosenyl group, tricosenyl group, tetracosenyl group, pentacosenyl group, hexacosenyl group, heptacosenyl group, octacosenyl group, nonacosenyl group, triacontenyl group, hentriacontenyl group, dotriacontenyl group, tritriacontenyl group, tetratriacontenyl group, pentatriacontenyl group, hexatriacontenyl group, heptatriacontenyl group, octatriacontenyl group, nonatriacontenyl group, tetracontenyl group, propanedienyl group, butadienyl group, pentadienyl group, hexadienyl group, heptadienyl group, octadienyl group, nonadienyl group, decadienyl group, undecadienyl group, dodecadienyl group, tridecadienyl group, tetradecadienyl group, pentadecadienyl group, hexadecadienyl group, heptadecadienyl group, octadecadienyl group, nonadecadienyl group, icosadienyl group, henicosadienyl group, docosadienyl group, tricosadienyl group, tetracosadienyl group, pentacosadienyl group, hexacosadienyl group, heptacosadienyl group, octacosadienyl group, nonacosadienyl group, triacontadienyl group, hentriacontadienyl group, dotriacontadienyl group, tritriacontadienyl group, tetratriacontadienyl group, pentatriacontadienyl group, hexatriacontadienyl group, heptatriacontadienyl group, octatriacontadienyl group, nonatriacontadienyl group, or tetracontadienyl group.

x simply needs to be a real number of 0 to 50. x is preferably a real number of 1 to 50, more preferably a real number of 4 to 45, even more preferably a real number of 8 to 40. x is preferably within the above range, as it makes it possible to produce an absorption promotor composition that is not separated and is stable during preparation.

y simply needs to be an integer of 1 to 5.

As a more suitable example of the oxa acid having a structure represented by the formula (2) above, $R^2$ is pentadecyl group, hexadecyl group, heptadecyl group, stearyl group (oxtadecyl group), nonadecyl group, icosyl group, henicosyl group, docosyl group, tricosyl group, tetracosyl group, pentacosyl group, hexacosyl group, heptacosyl group, octacosyl group, nonacosyl group, triacontyl group, hentriacontyl group, dotriacontyl group, tritriacontyl group, tetratriacontyl group, pentatriacontyl group, hexatriacontyl group, heptatriacontyl group, octatriacontyl group, nonatriacontyl group, tetracontyl group, pentadecenyl group, hexadecenyl group, heptadecenyl group, octadecenyl group, nonadecenyl group, icosenyl group, henicosenyl group, docosenyl group, tricosenyl group, tetracosenyl group, pentacosenyl group, hexacosenyl group, heptacosenyl group, octacosenyl group, nonacosenyl group, triacontenyl group, hentriacontenyl group, dotriacontenyl group, tritriacontenyl group, tetratriacontenyl group, pentatriacontenyl group, hexatriacontenyl group, heptatriacontenyl group, octatriacontenyl group, nonatriacontenyl group, tetracontenyl group, pentadecadienyl group, hexadecadienyl group, heptadecadienyl group, octadecadienyl group, nonadecadienyl group, icosadienyl group, henicosadienyl group, docosadienyl group, tricosadienyl group, tetracosadienyl group, pentacosadienyl group, hexacosadienyl group, heptacosadienyl group, octacosadienyl group, nonacosadienyl group, triacontadienyl group, hentriacontadienyl group, dotriacontadienyl group, tritriacontadienyl group, tetratriacontadienyl group, pentatriacontadienyl group, hexatriacontadienyl group, heptatriacontadienyl group, octatriacontadienyl group, nonatriacontadienyl group, or tetracontadienyl group, x is a real number of 1 to 20, and y is 1.

Such an oxa acid makes it possible to produce an absorption promotor composition that is not separated and is more stable during preparation and that is capable of improving the efficiency in absorption of a pharmaceutical drug, in particular a poorly absorbable pharmaceutical drug.

$R^2$ is a linear or branched hydrocarbon group having 1 to 40 carbon atoms. Alternatively, the oxa acid may suitably be an oxa acid in which $R^2$ is a cholesteryl group or preferably an oxa acid in which $R^2$ is a cholesteryl group, x is a real number of 1 to 20, and y is 1.

The oxa acid may be a commercially available compound. The oxa acid may be produced by, for example, the method described below. The method for producing the oxa acid is, however, not limited to the method described below.

First, cyclic lactone and an alcohol represented by the formula (3) below are subjected to esterification and etherification. Next, the product resulting from the reaction is hydrolyzed to produce a compound (carboxylic acid) which is represented by the formula (1) above and in which X represents —OH. Then, the carboxy group of the carboxylic acid produced is derivatized through esterification, amidation, or any of other various publicly known functional group mutually converting reaction to produce an oxa acid having a structure represented by the formula (1) above.

$$R^1-(OCH_2CH_2)_m-OH \qquad (3)$$

Specifically, an example method for producing an oxa acid having the structure represented by the formula (1) above includes at least (i) reacting cyclic lactone and an alcohol having a structure represented by the formula (3)

above with each other and (ii) hydrolyzing the product resulting from the step (i). The example method for producing an oxa acid having the structure represented by the formula (1) above may further include (iii) derivatizing the carboxyl group of the compound (carboxylic acid) which has resulted from the step (ii), which is represented by the formula (1), and in which X represents —OH.

The cyclic lactone for use in the step (i) is, for example, β-propiolactone, γ-butyrolactone, δ-valerolactone, or ε-caprolactone.

The oxa acid is preferably produced in such a manner that after the reaction described above has been carried out sufficiently, the resulting product is purified as appropriate by a publicly known method such as reduced-pressure distillation, silica gel chromatography, or crystallization. Purifying the product makes it possible to produce an oxa acid that is suitably usable as a promotor of absorption of a molecule having a biological function such as a physiologically active protein, a peptide, an antibody, a nucleic acid, and a low-molecular-weight pharmaceutical drug. Purifying the product also makes it possible to produce an oxa acid that is suitably usable as a promotor of absorption of a pharmaceutical drug carrier such as a liposome and a polymeric micelle.

An oxa acid in accordance with an embodiment of the present invention may cover in its scope a compound before the purification or a compound after the purification.

[2. Absorption Promotor Composition]

An absorption promotor composition in accordance with an embodiment of the present invention includes the absorption promotor and oil. An absorption promotor composition in accordance with an embodiment of the present invention may further include water. An absorption promotor composition in accordance with an embodiment of the present invention may include a surfactant in addition to the absorption promotor and the oil or in addition to the absorption promotor, the oil, and the water. An absorption promotor composition in accordance with an embodiment of the present invention may include a single kind of the absorption promotor or a plurality of kinds of the absorption promotor.

<2-1. Oil>

An absorption promotor composition in accordance with an embodiment of the present invention includes an absorption promotor and oil.

The oil may be a publicly known oil that allows a pharmaceutical drug to dissolve therein. Examples of the oil include (i) an oil such as vegetable oil, animal oil, mineral oil, and hardened oil thereof and (ii) a higher fatty acid. The absorption promotor composition may include only one kind of the oil or two or more kinds of the oil in combination.

Examples of the oil include (i) a vegetable oil such as avocado oil, olive oil, sesame oil, camellia oil, evening primrose oil, turtle oil, macadamia nut oil, corn oil, mink oil, rape-seed oil, yolk oil, persic oil, wheat germ oil, Camellia sasanqua oil, castor oil, linseed oil, safflower oil, cottonseed oil, perilla oil, soybean oil, peanut oil, tea seed oil, kaya oil, rice bran oil, tung oil, jojoba oil, cacao butter, and coconut oil and a hardened oil thereof, (ii) an animal oil such as horse oil, beef tallow, mutton tallow, lard, lanolin, and spermaceti, and a hardened oil thereof, and (iii) a mineral oil such as liquid paraffin and vaseline, and a hardened oil thereof. The oil is preferably soybean oil or rape-seed oil, more preferably soybean oil.

Examples of the higher fatty acid include caproic acid, caprylic acid, capric acid, lauric acid, myristic acid, palmitic acid, oleic acid, linoleic acid, linolenic acid, and stearic acid. The higher fatty acid is preferably myristic acid, oleic acid, or linolenic acid, more preferably oleic acid.

The oil may be contained in any amount that allows a pharmaceutical drug described later to dissolve. The oil is contained in an amount of preferably 10% by weight to 150% by weight, more preferably 20% by weight to 100% by weight, even more preferably 40% by weight to 80% by weight, relative to the absorption promotor.

<2-2. Water>

An absorption promotor composition in accordance with an embodiment of the present invention may include water in addition to an absorption promotor and oil. The term "water" as used herein refers to a diluent component.

The term "water" refers not only to so-called water such as ultrapure water (MilliQ [registered trademark] water), distilled water, and ion-exchange water, but also to any of various buffer solutions such as a phosphate buffer solution and physiological saline.

In a case where an absorption promotor composition in accordance with an embodiment of the present invention includes the absorption promotor, oil, and water, the absorption promotor may be contained in any amount that allows a pharmaceutical drug to be emulsified. The absorption promotor is contained in an amount of preferably 5% by weight to 20% by weight, more preferably 10% by weight to 20% by weight, even more preferably 15% by weight to 20% by weight, relative to the total weight of the absorption promotor, oil, and water. The oil may be contained in any amount that allows a pharmaceutical drug described later to dissolve. The oil is contained in an amount of preferably 5% by weight to 30% by weight, more preferably 5% by weight to 20% by weight, even more preferably 5% by weight to 15% by weight, relative to the total weight of the absorption promotor, oil, and water. The water is contained in an amount of preferably 50% by weight to 90% by weight, more preferably 55% by weight to 85% by weight, even more preferably 60% by weight to 80% by weight, relative to the total weight of the absorption promotor, oil, and water.

The oxa acid and the oil form micelles. Specifically, a pharmaceutical drug is dissolved in the oil, and the oil is surrounded by oxa acid molecules each with its hydrophobic group positioned inside, so that micelles are formed. This allows a pharmaceutical drug to be emulsified.

The micelles have an average particle diameter of preferably not more than 1000 nm, more preferably not more than 600 nm, even more preferably not more than 400 nm, particularly preferably not more than 200 nm. The micelles preferably have an average particle diameter of not more than 1000 nm, as such an average particle diameter makes it possible to improve the efficiency in absorption of a pharmaceutical drug, in particular a poorly absorbable pharmaceutical drug. The average particle diameter of micelles is measured with use of Zetasizer Nano ZS (available from Malvern Institutes) in the measurement mode "size-small-vol-cell×1.SOP".

The absorption promotor composition preferably contains micelles not less than 5% of which have a particle diameter of not more than 100 nm. The absorption promotor composition contains micelles more preferably not less than 10%, even more preferably not less than 15%, of which have a particle diameter of not more than 100 nm. An absorption promotor composition containing micelles each with a particle diameter within the above range improves the efficiency in absorption of a pharmaceutical drug, in particular a poorly absorbable pharmaceutical drug. The proportion of micelles each with a particle diameter of not more than 100 nm relative to the total number of micelles is calculated from a peak area in a particle size distribution measured with use of Zetasizer Nano ZS (available from Malvern Institutes) in the measurement mode "size-small-vol-cell×1.SOP".

<2-3. Surfactant>

An absorption promotor composition in accordance with an embodiment of the present invention may include a surfactant in addition to the absorption promotor and the oil or in addition to the absorption promotor, the oil, and the water.

The surfactant may be a publicly known surfactant. The absorption promotor composition may include only one kind of the surfactant or two or more kinds of the surfactant in combination.

Examples of the surfactant include a polysorbate such as Tween (registered trademark) 20 (polyoxyethylene (20) sorbitan monolaurate), Tween (registered trademark) 80 (polyoxyethylene (20) sorbitan monooleate), and Tween (registered trademark) 85 (polyoxyethylene sorban trioleate); a polyoxyethylene castor oil such as Cremophor (registered trademark) EL; a polyethyleneglycol such as PEG and PEG 400; and a propyleneglycol, a glycerol, and Transcutol (registered trademark) P (diethylene glycol monoethyl ether).

The surfactant is contained in an amount of preferably 5% by weight to 100% by weight, more preferably 10% by weight to 80% by weight, even more preferably 20% by weight to 60% by weight, relative to the total weight of the absorption promotor composition.

<2-4. Other Components>

The absorption promotor composition may include as necessary a stabilization agent, a pH adjusting agent, an antioxidant, and/or another reagent(s). Examples of the stabilization agent include sodium benzoate and glycine. Examples of the pH adjusting agent include citric acid and sodium acid carbonate. Examples of the antioxidant include L-ascorbic acid and tocopherol.

<2-5. Method for Producing Absorption Promotor Composition>

An absorption promotor composition in accordance with an embodiment of the present invention may be produced through, for example, steps of (i) stirring an absorption promotor and oil, (ii) adding water to the absorption promotor and the oil, and (iii) heating and stirring the absorption promotor, the oil, and the water until the temperature of the mixture reaches 80° C.

The step (i) is a step of stirring an absorption promotor and oil. An absorption promotor and oil may be stirred by any method that allows the absorption promotor to be dissolved in the oil. The stirring may be carried out with use of, for example, a conventionally publicly known mixing device such as a vortex mixer or a homogenizer.

The step (ii) is a step of adding water to the absorption promotor and the oil. The step (ii) may involve adding water in its entirety at a time, or in a plurality of separate portions while the mixture is being stirred.

The step (ii) may be carried out simultaneously with the step (i) or after the step (i). The step (ii) is carried out preferably simultaneously with the step (i), as it allows the absorption promotor to be dissolved in the oil easily, and makes it possible to produce a uniform absorption promotor composition.

The step (iii) is a step of heating and stirring the absorption promotor, the oil, and the water until the temperature of the mixture reaches 80° C. The step (iii) is preferably carried out, as that makes it possible to produce an absorption promotor composition that is not separated during preparation and that is uniformly emulsified.

The step (iii) involves heating the mixture until the liquid temperature reaches preferably 100° C., more preferably 80° C., even more preferably 70° C.

A method for producing an absorption promotor composition in accordance with an embodiment of the present invention includes the above steps (i), (ii), and (iii). Another embodiment of the method may include the steps (i) and (ii) only.

[3. Absorption Promotor Kit]

An absorption promotor kit in accordance with an embodiment of the present invention simply needs to include at least an absorption promotor in accordance with an embodiment of the present invention and the oil. The description below avoids repeating the same matters already described under [1. Absorption promotor] and [2. Absorption promotor composition], and refers back to such matters as appropriate.

The term "kit" as used herein is intended to mean that at least one of various components is contained in a separate container. More specifically, the term "kit" refers to, for example, a package including a container (for example, a bottle, a plate, a tube, or a dish) that contains a particular ingredient(s). A kit is preferably accompanied by an instruction manual on how to use the ingredient. Such an instruction manual may be written or printed on a medium such as paper or stored on an electronic medium such as a magnetic tape, a computer-readable disc or tape, or a CD-ROM.

The absorption promotor kit is typically packaged in appropriate form. In a case where the ingredient is a solid drug, the absorption promotor kit is often put in an extrusion package made of plastic and/or metal.

The absorption promotor kit may include an absorption promotor and oil in the same container, or in separate containers so that the absorption promotor and the oil are mixed with each other immediately before use.

The absorption promotor kit may include a container that contains a stabilization agent, a pH adjusting agent, an antioxidant, and/or another reagent(s).

[4. Pharmaceutical Composition]

A pharmaceutical composition in accordance with an embodiment of the present invention includes at least an absorption promotor in accordance with an embodiment of the present invention and a pharmaceutical drug.

The term "pharmaceutical drug" as used herein refers to any substance for use in inhibiting, diagnosing, alleviating, treating, curing, or preventing a disease or disease condition. Examples of the pharmaceutical drug include a medicinal composition and a functional food. The term "functional food" as used herein refers to a perishable foodstuff or processed food having a disease preventive property and/or health promotion property. The functional food is also referred to as "nutrition-supplement food".

The pharmaceutical drug is not limited to any particular one. The pharmaceutical drug is, in particular, preferably a poorly absorbable pharmaceutical drug, as the present invention produces a remarkable effect in that case. More specifically, the pharmaceutical drug is preferably a pharmaceutical drug that belongs to Class 4 of the BSC classification. Examples of the pharmaceutical drug include, but are not limited to, terfenadine, furosemide, ciclosporin, acetazolamide, colistin, mebendazole, albendazole, coenzyme Q10 (herein also referred to as "CoQ10"), curcumin, and lutein.

A pharmaceutical drug that belongs to Class 4 of the BSC classification characteristically has low solubility and low membrane permeability. The use of an absorption promotor composition including an oxa acid having a particular structure and oil, however, makes it possible to emulsify even a pharmaceutical drug that belongs to Class 4 of the BSC classification.

A pharmaceutical drug can be contained in the pharmaceutical composition in an amount that is determined as appropriate in view of, for example, the form and method of administration.

Examples of the dosage form of the pharmaceutical composition include an oral preparation such as a tablet, a capsule (for example, a soft capsule and a microcapsule), powder, a granule, and syrup; and a parenteral preparation such as an injection, a suppository, a pellet, and a drop.

The pharmaceutical composition is administered in an amount that is not fixed and is determined as appropriate according to the formulation, the administration method, and the purpose of use as well as the age, body weight, and symptoms of the patient to which the pharmaceutical drug is to be administered. A person skilled in the art can select optimal conditions as appropriate according to, for example, the administration target, the route of administration, or the symptoms.

The pharmaceutical composition can be administered through an appropriate route of administration according to the formulation. The administration method is not limited to any particular one. The pharmaceutical composition may be taken internally, externally, or by injection. The injection may be administered, for example, intravenously, intramuscularly, subcutaneously, or intracutaneously.

EXAMPLES

The following will describe the present invention in greater detail on the basis of Examples. The present invention is, however, not limited to the Examples below.

[Preparing Absorption Promotor Composition]

Example 1

First, 48 g of chloroacetic acid (available from Tokyo Chemical Industry Co., Ltd.) and 250 g of polyethylenegly-col monooleyl ether (available from Sigma-Aldrich, product name: Brij [registered trademark] O10) were charged into a reaction container together with 62 g of KOH and 800 mL of toluene. The mixture was stirred at 40° C. to 100° C. for 24 hours for condensation polymerization. This step produced an oxa acid (1) (HLB value: 2.005) which had a structure represented by the formula (4) below and in which p was 1.9 on average.

Next, 0.12 g of soybean oil (available from Wako Pure Chemical Industries, Ltd.) and 0.036 g of the oxa acid (1) were stirred in a vortex mixer for 10 seconds. Then, ultrapure water (MilliQ [registered trademark] water) was added to the resulting mixture five times in an amount of 88.8 µL each time. Each time of the addition, the mixture was, while being kept cold with use of ice, stirred in an ultrasonic homogenizer at a cycle of 1.0 and an amplitude of 40% under a stirring condition corresponding to the number of stirring operations (that is, how many times the ultrapure water was added). This produced an absorption promotor composition of Example 1. Table 1 below shows the stirring conditions.

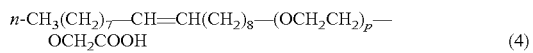

(4)

TABLE 1

| Number of stirring operations | Stirring time (sec) | Time to next stirring (sec) |
|---|---|---|
| First time | 10 | 20 |
| Second time | 20 | 40 |
| Third time | 30 | 60 |
| Fourth time | 30 | 60 |
| Fifth time | 30 | — |

Example 2

First, 35 g of chloroacetic acid (available from Tokyo Chemical Industry Co., Ltd.) and 250 g of polyethyleneglycol monooleyl ether (available from Aoki Oil Industrial Co., Ltd, product name: Blaunon EN-905) were charged into a reaction container together with 46 g of KOH and 800 mL of toluene. The mixture was stirred at 40° C. to 100° C. for 24 hours for condensation polymerization. This step produced an oxa acid (2) (HLB value: 2.994) which had a structure represented by the formula (4) above and in which p was 4.9 on average.

An absorption promotor composition of Example 2 was produced as in Example 1 except that 0.036 g of the oxa acid (2) was used.

Example 3

First, 24 g of chloroacetic acid (available from Tokyo Chemical Industry Co., Ltd.) and 250 g of polyethyleneglycol monooleyl ether (available from Sigma-Aldrich, product name: Brij [registered trademark] 93) were changed into a reaction container together with 32 g of KOH and 800 mL of toluene. The mixture was stirred at 40° C. to 100° C. for 24 hours for condensation polymerization. This step produced an oxa acid (3) (HLB value: 4.334) which has a structure represented by the formula (4) above and in which p is 9.0 on average.

An absorption promotor composition of Example 3 was produced as in Example 1 except that 0.036 g of the oxa acid (3) was used.

Example 4

First, 0.6 g of soybean oil (available from Wako Pure Chemical Industries, Ltd.), 0.9 g of the oxa acid (3), and 4.5 mL of ultrapure water were put into a vial. The mixture was stirred with use of a hot stirrer until the liquid temperature reached 70° C. to 80° C. The resulting mixture was put into another stirrer and let stand to cool. The mixture was then rapidly cooled to room temperature while being stirred and kept cold with use of ice. This produced an absorption promotor composition of Example 4.

Example 5

An absorption promotor composition of Example 5 was produced as in Example 4 except that 0.6 g of the oxa acid (3) and 4.8 mL of ultrapure water were used.

Example 6

An absorption promotor composition of Example 6 was produced as in Example 4 except that 4.125 mL of ultrapure water and 375 µL of PEG 400 were used in place of 4.5 mL of ultrapure water.

[Measuring Particle Diameters of Micelles in Absorption Promotor Composition and Polydispersity Index (PDI) of Absorption Promotor Composition]

First, 70 μL of the absorption promotor composition produced in each of Examples 1 to 6 was taken. The particle diameters of micelles in the absorption promotor composition were measured with use of Zetasizer Nano ZS (available from Malvern Instruments). The PDI was measured in the measurement mode "size-small-vol-cell×1.SOP" of Zetasizer Nano ZS. Further, the particle diameters of micelles were measured on the basis of the Z-average value. Six measurements were made with use of different samples. The average was used as the average particle diameter of the micelles. Table 2 shows the analysis results.

produced a pharmaceutical composition containing CoQ10. Next, 1 g/kg of the pharmaceutical composition produced was orally administered into the rat with use of a gastric tube so that CoQ10 was administered in an amount of 25 mg per kilogram of the body weight. Then, 350 μL of blood was collected from the jugular vein 0 hours, 0.5 hours, 1 hour, 2 hours, 3 hours, 4 hours, 5 hours, 6 hours, 9 hours, 12 hours, 24 hours, and 48 hours after the oral administration of the pharmaceutical composition. The blood collected was immediately mixed with a trace amount of heparin sodium. The mixture was centrifuged at 750×g and 4° C. for 10 minutes. Then, 100 μL of the supernatant was taken for use as a CoQ10 blood plasma sample.

TABLE 2

|  |  | Example 1 | Example 2 | Example 3 | Example 4 | Example 5 | Example 6 |
|---|---|---|---|---|---|---|---|
| Soybean oil | Prepared amount | 0.12 g | 0.12 g | 0.12 g | 0.6 g | 0.6 g | 0.6 g |
|  | Weight proportion (%) | 20 | 20 | 20 | 10 | 10 | 10 |
| Oxa acid | Kind | Oxa acid (1) | Oxa acid (2) | Oxa acid (3) | Oxa acid (3) | Oxa acid (3) | Oxa acid (3) |
|  | Prepared amount | 0.036 g | 0.036 g | 0.036 g | 0.9 g | 0.6 g | 0.9 g |
|  | Weight proportion (%) | 6 | 6 | 6 | 15 | 10 | 15 |
| Ultra-pure water | Prepared amount | 0.444 g | 0.444 g | 0.444 g | 4.5 mL | 4.8 mL | 4.125 mL |
|  | Weight proportion (%) | 74 | 74 | 74 | 75 | 80 | 68.75 |
| PEG 400 | Prepared amount | — | — | — | — | — | 375 μL |
|  | Weight proportion (%) |  |  |  |  |  | 6.25 |
| Average particle diameter (nm) |  | 144.4 | 280.1 | 208.2 | 52.53 | 3873 | 64.56 |
| PDI |  | 0.620 | 0.609 | 0.510 | 1.000 | 0.293 | 1.000 |

As Table 2 shows, the respective average particle diameters of micelles in the respective absorption promotor compositions of Examples 1 to 6 were 144.4 nm, 280.1 nm, 208.2 nm, 52.53 nm, 3873 nm, and 64.56 nm. Example 4 resulted in preparation of an absorption promotor composition containing micelles having small particle diameters of 52.53 ±14.2 nm.

As Table 2 shows, the respective PDIs of the respective absorption promotor compositions of Examples 1 to 6 were 0.620, 0.609, 0.510, 1.000, 0.293, and 1.000.

[Oral Administration of CoQ10]

Examples 7 to 10

Orally Administering CoQ10 with Use of Respective Absorption Promotor Compositions of Examples 1 to 4

A male Wistar rat (7 to 9 weeks old) was forced to fast overnight (14 hours to 16 hours), and was then anesthetized with use of diethyl ether. After the anesthetization, the neck of the rat was partially incised for exposure of a jugular vein.

CoQ10 (available from Wako Pure Chemical Industries, Ltd., product name: Ubiquinone-10) in an amount of 25 mg was added to 1 g of the absorption promotor composition of each of Examples 1 to 4. The mixture was then stirred. This To determine the concentration of CoQ10 in the blood plasma, a HPLC sample of CoQ10 was prepared as follows: First, 100 μL of hexane and 400 μL of methanol were added to 100 μL of the CoQ10 blood plasma sample. The mixture was stirred in a vortex mixer for 30 seconds. After that, 2 mL of hexane was further added. The mixture was stirred in a vortex mixer for 30 seconds. Then, the mixture was centrifuged at 2330×g and 20° C. for 10 minutes. Then, 1.8 mL of the organic phase was taken, and was evaporated at 40° C. for 30 minutes to be dried. Then, 100 μL of an eluant (described later) was added to the residue from the evaporation to dryness. The mixture was stirred in a vortex mixer for 10 seconds. The resulting product was used as a HPLC sample of CoQ10. The HPLC measurement conditions for CoQ10 were as follows:

Column: Inertsil ODS-4 (3.0×150 mm)

Eluant: Methanol:ethanol=35:65 (v/v)

Flow rate: 0.4 mL/min

Wavelength: UV 275 nm

Column temperature: 40° C.

Injection volume: 40 μL

The absorption promotor composition of Example 1 was used for Example 7. The absorption promotor composition of Example 2 was used for Example 8. The absorption promotor composition of Example 3 was used for Example 9. The absorption promotor composition of Example 4 was used for Example 10.

Comparative Example 1

A CoQ10 blood plasma sample of Comparative Example 1 was prepared as in Examples 7 to 10 above except that for administration of CoQ10, the absorption promotor composition of each of Examples 1 to 4 was replaced with an emulsion prepared by (i) adding, as emulsifiers, 5 mM of sodium taurocholate and 40 µM of phosphatidylcholine (with an assumed molecular weight of approximately 700) to isopropyl myristate, (ii) finally adding ultrapure water (MilliQ [registered trademark] water) to the mixture, and (iii) stirring the resulting mixture. The CoQ10 concentration of the CoQ10 blood plasma sample prepared was measured as in Examples 7 to 10.

Comparative Example 2

A CoQ10 blood plasma sample of Comparative Example 2 was prepared as in Examples 7 to 10 except that for administration of CoQ10, the absorption promotor composition of each of Examples 1 to 4 was not used so that only the base powder of CoQ10 was administered. The base powder of CoQ10 was suspended in 0.5% methyl cellulose before being orally administered to a rat with use of a gastric tube so that CoQ10 was administered in an amount of 25 mg per kilogram of the body weight. The CoQ10 concentration of the CoQ10 blood plasma sample prepared was measured as in Examples 7 to 10.

(Results)

(a) of FIG. 1 is a graph that shows how the concentration of CoQ10 in blood plasma changed in Example 7 (which involved use of the absorption promotor composition of Example 1). (b) of FIG. 1 is a graph that shows how the concentration of CoQ10 in blood plasma changed in Example 8 (which involved use of the absorption promotor composition of Example 2). (c) of FIG. 1 is a graph that shows how the concentration of CoQ10 in blood plasma changed in Example 9 (which involved use of the absorption promotor composition of Example 3). (d) of FIG. 1 is a graph that shows how the concentration of CoQ10 in blood plasma changed in Example (which involved use of the absorption promotor composition of Example 4). (a) of FIG. 2 is a graph that shows how the concentration of CoQ10 in blood plasma changed in Comparative Example 2 (which involved administration of CoQ10 only). (b) of FIG. 2 is a graph that shows how the concentration of CoQ10 in blood plasma changed in Comparative Example 1 (which involved use of sodium taurocholate and phosphatidylcholine as emulsifiers). In (a) to (d) of FIG. 1 and (a) and (b) of FIG. 2, each symbol indicates the average of an individual sample, whereas each line indicates the standard deviation. (a) to (d) of FIG. 1 each shows the results of measurement involving five to six samples. (a) and (b) of FIG. 2 each show the results of measurement involving three to six samples.

The concentration of CoQ10 in blood plasma was increased in Examples 7 to 10 (which involved use of the respective absorption promotor compositions of Examples 1 to 4). This indicates an improvement in bioavailability. A comparison between Examples 9 and 10 shows that CoQ10 was absorbed in a larger amount in the case (Example 10) involving use of the absorption promotor composition of Example 4, in which the average particle diameter of micelles was smaller. This should indicate that CoQ10 is absorbed with a higher efficiency in a case where the average particle diameter of micelles in an absorption promotor composition is smaller. CoQ10 was absorbed in a larger amount in Comparative Example 1 as well (which involved use of sodium taurocholate and phosphatidylcholine as emulsifiers), but the increase was slight.

The above results prove that emulsifying CoQ10 with use of any of the respective absorption promotor compositions of Examples 1 to 4 increases the efficiency in absorption of CoQ10.

[Oral Administration of Curcumin]

Example 11

Orally Administering Curcumin with Use of Absorption Promotor Composition of Example 6

A male Wistar rat (7 to 9 weeks old) was forced to fast overnight (14 hours to 16 hours), and was then anesthetized with use of diethyl ether. After the anesthetization, the neck of the rat was partially incised for exposure of a jugular vein.

Curcumin (available from Tokyo Chemical Industry Co., Ltd., product name: Curcumin) in an amount of 3 mg was added to 1 g of the absorption promotor composition of Example 6. The mixture was then stirred. This produced a pharmaceutical composition containing curcumin. Next, 3 g/kg of the pharmaceutical composition produced was orally administered into the rat with use of a gastric tube so that curcumin was administered in an amount of 10 mg per kilogram of the body weight. Then, 600 µL of blood was collected from the jugular vein 0 minutes, 15 minutes, 30 minutes, 1 hour, 2 hours, 3 hours, 4 hours, 6 hours, 9 hours, 12 hours, and 24 hours, after the oral administration of the pharmaceutical composition. The blood collected was immediately mixed with a trace amount of heparin sodium. The mixture was centrifuged at 750×g and 4° C. for 10 minutes. Then, 200 µL of the supernatant was taken. Next, 25 µL of 1% formic acid was added to the above-taken supernatant for use of the mixture as a curcumin blood plasma sample. The curcumin blood plasma sample was stored at −20° C. until measurement.

To determine the concentration of curcumin in the blood plasma, a HPLC sample of curcumin was prepared as follows: First, 200 µL of 0.1M sodium acetate containing 6000 U/mL of β-glucuronidase was added to 200 µL of the curcumin blood plasma sample. The mixture was incubated at 37° C. for 2 hours. After that, 10 of a 10 µL/mL emodin methanol solution and 10 µL of methanol were added to the mixture. The resulting mixture was stirred in a vortex mixer for 10 seconds, and was then centrifuged at 18800×g for 10 minutes. After that, 1.25 mL of ethyl acetate was added to the mixture. The resulting mixture was stirred in a vortex mixer for 10 minutes. Then, 1 mL of the supernatant was taken, and was evaporated at 40° C. for 30 minutes to be dried. Then, 100 µL of 80% acetonitrile was added to the residue from the evaporation to dryness. The mixture was stirred in a vortex mixer for 60 seconds. The resulting product was used as a HPLC sample of curcumin. The HPLC measurement conditions for curcumin were as follows:

Column: Inertsil ODS-4 (3.0×150 mm)
Eluant: acetonitrile:tetrahydrofuran:0.1% formic acid=35:20:45 (v/v/v)
Flow rate: 0.3 mL/min
Wavelength: 425 nm
Column temperature: 40° C.
Injection volume: 20 µL

Comparative Example 3

A curcumin blood plasma sample was prepared as in Example 11 except that for oral administration of curcumin in Example 11, the absorption promotor composition of Example 6 was not used so that only the base powder of curcumin was administered. The base powder of curcumin was suspended in 0.5% methyl cellulose before being orally administered to a rat with use of a gastric tube so that curcumin was administered in an amount of 100 mg per kilogram of the body weight. The curcumin concentration of the curcumin blood plasma sample prepared was measured as in Example 11.

(Results)

(a) of FIG. 3 is a graph that shows how the concentration of curcumin in blood plasma changed in Example 11 (which involved use of the absorption promotor composition of Example 6). (b) of FIG. 3 is a graph that shows how the concentration of curcumin in blood plasma changed in comparative Example 3 (which involved administration of curcumin only). The concentration of curcumin in blood plasma was increased in the case involving use of the absorption promotor composition of Example 6. This indicates an improvement in bioavailability. Further, Example 11 shows that an absorption promotor composition in accordance with an embodiment of the present invention is capable of improving the efficiency in absorption of not only a poorly absorbable pharmaceutical drug having a long alkyl chain such as CoQ10 but also a poorly absorbable pharmaceutical drug free from a long alkyl chain such as curcumin.

[Calculating Pharmacokinetics Parameters]

Pharmacokinetics parameters were calculated about how the concentration of CoQ10 in blood plasma changed in each of Examples 7 to 10, which involved use of the respective absorption promotor compositions of Examples 1 to 4.

For calculation of pharmacokinetics parameters, parameters $C_{max}$ and $T_{max}$ were obtained with use of the results of how the concentration of CoQ10 in blood plasma changed. The $AUC_{0-48hr}$ value (AUC: area under the curve) was determined on the basis of the trapezoidal rule. The $ABS_{0-48hr}$ value ($ABS_{0-48hr} = AUC_{0-48hr} - C_0 \times 48$) was calculated for exclusion of endogenous contribution.

(a) of FIG. 4 is a graph that compares $ABS_{0-48hr}$ values about how the concentration of CoQ10 in blood plasma changed in Examples 7 to 10, which involved use of the respective absorption promotor compositions of Examples 1 to 4. (b) of FIG. 4 is a graph that compares $C_{max}$ values about how the concentration of CoQ10 in blood plasma changed in Examples 7 to 10, which involved use of the respective absorption promotor compositions of Examples 1 to 4. (c) of FIG. 4 is a graph that compares $T_{max}$ values about how the concentration of CoQ10 in blood plasma changed in Examples 7 to 10, which involved use of the respective absorption promotor compositions of Examples 1 to 4. In (a) to (c) of FIG. 4, each bar indicates the average of five to six samples, whereas each line indicates the standard deviation. In particular, Examples 9 and 10 (which involved use of the respective absorption promotor compositions of Examples 3 and 4) had high values for $ABS_{0-48hr}$ and $C_{max}$, each of which is an indicator of exogenous contribution for CoQ10 absorption. This should indicate that an absorption promotor composition including an oxa acid contributes greatly to improvement in the efficiency in absorption of CoQ10.

[Evaluating Stability of Absorption Promotor Composition]

The respective absorption promotor compositions of Examples 1 to 4 and 6 were each diluted 50-fold with water, a fasted state simulated gastric fluid (FaSSGF), or a fasted state simulated intestinal fluid (FaSSIF), and were then each incubated at 37° C. for 3 hours. This produced a diluent. During the incubation, each absorption promotor composition was stirred in a vortex mixer every 30 minutes. The FaSSGF and the FaSSIF were each prepared on the basis of N Heshmati et al., In Vitro and in Vivo Evaluations of the Performance of an Indirubin Derivative, Formulated in Four Different Self-Emulsifying Drug Delivery Systems, J Pharm Pharmacol 66 (11), 1567-1575, 2014 to have the composition below. The FaSSGF had a pH of 1.6 as adjusted with use of hydrochloric acid. The FaSSIF had a pH of 6.5 as adjusted with use of sodium hydroxide.

<Composition of FaSSGF>
Sodium taurocholate 0.08 mM
Lecithin 0.02 mM
Pepsin 0.051 U/mL
Sodium chloride 34.2 mM
<Composition of FaSSIF>
Sodium taurocholate 3 mM
Lecithin 0.75 mM
Sodium dihydrogen phosphate 28.36 mM
Sodium chloride 105.85 mM After the adjustment, 70 µL of each diluent was taken. The particle diameters of micelles in each of the respective absorption promotor compositions of Examples 1 to 4 and 6 were measured with use of Zetasizer Nano ZS (available from Malvern Instruments). The particle diameters of micelles were measured in the measurement mode "size-small-vol-cell×1.SOP" of Zetasizer Nano ZS on the basis of the Z-average value. Three measurements were made with use of different samples. The average was used as the average particle diameter of the micelles. (a) of FIG. 5 is a graph that shows the average particle diameter of micelles in each of the respective absorption promotor compositions of Examples 1 to 3 for cases where each of the absorption promotor compositions was incubated with use of water, a FaSSGF, or a FaSSIF. (b) of FIG. 5 is a graph that shows the average particle diameter of micelles in each of the respective absorption promotor compositions of Examples 2 and 3 for cases where each of the absorption promotor compositions was incubated with use of water, a FaSSGF, or a FaSSIF. (c) of FIG. 5 is a graph that shows the average particle diameter of micelles in the absorption promotor composition of Example 4 for cases where the absorption promotor composition was incubated with use of water, a FaSSGF, or a FaSSIF. (d) of FIG. 5 is a graph that shows the average particle diameter of micelles in the absorption promotor composition of Example 6 for cases where the absorption promotor composition was incubated with use of water, a FaSSGF, or a FaSSIF. In (a) to (d) of FIG. 5, each line indicates the standard deviation. (a) of FIG. 5 shows that the average particle diameter of micelles in the absorption promotor composition of Example 1 as incubated with use of a FaSSGF was larger than that immediately after the preparation. The absorption promotor composition of Example 1, after oral administration, breaks down and then agglomerates in the stomach. This should indicate that the average particle diameter of the micelles is approximately 6000 nm in a low pH environment that simulates the inside of the stomach. After that, the absorption promotor composition of Example 1 is presumed to be mixed with a bile component such as sodium taurocholate in intestinal juice to be minute. The resulting smaller particles then reach the small intestine. (b) of FIG. 5 shows that the average particle diameter of micelles in the absorption promotor composition of Example 2 as incubated with use of a FaSSGF was approximately 2.4 times larger than that immediately after the preparation. (b) and (c) of FIG. 5 show that the average particle diameter of micelles in each of the respective absorption promotor compositions of Examples 3 and 4 as incubated with use of a FaSSGF or a FaSSIF was not much different from that immediately after the preparation. This should indicate that micelles in each of the respective absorption promotor compositions of Examples 3 and 4 reach the small intestine while, even after oral administration, stably maintaining the average particle diameter that the micelles had immediately after the preparation. (d) of FIG. 5 shows that while the average particle diameter of micelles in the absorption promotor composition of Example 6 was slightly larger than the average particle diameter of micelles in the absorption promotor composition of Example 4 immediately after the preparation, the two average particle diameters were substantially equal to each other after the incubation with water, a FaSSGF, or a FaSSIF. This indicates that an absorption promotor composition containing PEG 400 also has excellent stability with respect to a FaSSGF and a FaSSIF.

[Observing Change of Particles of Absorption Promotor Composition with Use of Absorption Predicting System]

The absorption predicting system illustrated in FIG. 6 was used to observe how absorption promotor composition particles change. A FaSSGF and a FaSSIF were heated to 37° C., and were caused to flow at a flow rate of 0.5 mL/min with use of a three-tubed pump. The FaSSGF was caused to flow into the Stomach container. The FaSSIF was caused to flow into the Intestine container. The FaSSIF was adjusted so as to have a pH of 6.0 to 7.0 when mixed with an equal amount of the FaSSGF. After the Intestine container was filled with the FaSSIF, 100 µL of each of the respective absorption promotor compositions of Examples 1, 2, 3, 4, and 6 was put into the Stomach container, and was stirred. After the stirring, the solution in the Intestine container was sampled every 5 minutes. Then, 70 µL of the sampled solution was taken. Further, the particle diameters of micelles in the above-taken solution were measured in the measurement mode "size-small-vol-cellx1.SOP" of Zetasizer Nano ZS on the basis of the Z-average value. Three measurements were made with use of different samples (one measurement for Example 6). The average was used as the average particle diameter of the micelles.

(a) of FIG. 7 is a graph that shows the average particle diameter, during each time frame, of micelles in each of the respective absorption promotor compositions of Examples 1 to 3 that has passed through a FaSSGF and a FaSSIF. (b) of FIG. 7 is a graph that shows the average particle diameter, during each time frame, of micelles in each of the respective absorption promotor compositions of Examples 2 and 3 that has passed through a FaSSGF and a FaSSIF. (c) of FIG. 7 is a graph that shows the average particle diameter, during each time frame, of micelles in the absorption promotor composition of Example 4 that has passed through a FaSSGF and a FaSSIF. (d) of FIG. 7 is a graph that shows the average particle diameter, during each time frame, of micelles in each of the absorption promotor composition of Example 6 that has passed through a FaSSGF and a FaSSIF. In (a) to (d) of FIG. 7, each line indicates the standard deviation. (a) of FIG. 7 shows that the average particle diameter of micelles in the absorption promotor composition of Example 1 was smaller than the average particle diameter of micelles in the absorption promotor composition of Example 2 and the average particle diameter of micelles in the absorption promotor composition of Example 3 immediately after the preparation, but was larger than the average particle diameter of micelles in the absorption promotor composition of Example 2 and the average particle diameter of micelles in the absorption promotor composition of Example 3 after having passed through a FaSSGF and a FaSSIF. (b) of FIG. 7 shows that the average particle diameter of micelles in each of the respective absorption promotor compositions of Examples 2 and 3 did not change much as a result of having passed through a FaSSGF and a FaSSIF. (b) of FIG. 7 also shows that the average particle diameter of micelles in the absorption promotor composition of Example 3 had a standard deviation smaller than that of the average particle diameter of micelles in the absorption promotor composition of Example 2. This should indicate that the micelles in the absorption promotor composition of Example 3 each maintained its small particle diameter in the small intestine more stably.

(a) of FIG. 8 is a graph that shows the particle size distribution of micelles in the absorption promotor composition of Example 1 that has passed through a FaSSGF and a FaSSIF. (b) of FIG. 8 is a graph that shows the particle size distribution of micelles in the absorption promotor composition of Example 2 that has passed through a FaSSGF and a FaSSIF. (c) of FIG. 8 is a graph that shows the particle size distribution of micelles in the absorption promotor composition of Example 3 that has passed through a FaSSGF and a FaSSIF. (d) of FIG. 8 is a graph that shows the particle size distribution of micelles in the absorption promotor composition of Example 4 that has passed through a FaSSGF and a FaSSIF. (e) of FIG. 8 is a graph that shows the particle size distribution of micelles in the absorption promotor composition of Example 6 that has passed through a FaSSGF and a FaSSIF. (a) to (e) of FIG. 8 each show the results of adding the absorption promotor composition of the corresponding one of Examples 1 to 4 and 6 into the Stomach container, stirring the absorption promotor composition, and then sampling a portion of the absorption promotor composition during the time frame of 25 minutes to 30 minutes after the stirring. (a) of FIG. 8 shows that the absorption promotor composition of Example 1 contained micelles 6% of which had a particle diameter of not more than 100 nm. (b) of FIG. 8 shows that the absorption promotor composition of Example 2 contained micelles most of which had a particle diameter of approximately 200 nm to 600 nm. (c) of FIG. 8 shows that the absorption promotor composition of Example 3 contained micelles 8.5% of which had a particle diameter of not more than 100 nm. (d) of FIG. 8 shows that the absorption promotor composition of Example 4 contained micelles 19.6% of which had a particle diameter of not more than 100 nm and which included micelles each having a small particle diameter of approximately 20 nm. (e) of FIG. 8 shows that the absorption promotor composition of Example 6 contained micelles 16.5% of which had a particle diameter of not more than 100 nm and which included micelles each having a small particle diameter of approximately 20 nm.

Industrial Applicability

The present invention is applicable as a method for improving the efficiency in absorption of a pharmaceutical drug in such fields as health care and health food, and is applicable in particular as a method for improving the efficiency in absorption of, for example, a poorly absorbable pharmaceutical drug.

The invention claimed is:

1. An oral preparation comprising:
an absorption promotor containing an oxa acid having a structure represented by formula (A) below,

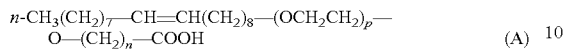

(A)

where p on average is a real number of 1 to 9, and n is an integer of 1 to 5;

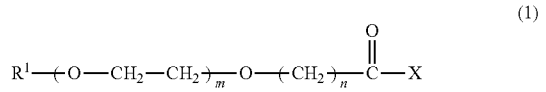

(1)

soybean oil; and
a drug,
wherein the oral preparation is a capsule, a powder, a granule, a syrup, or a liquid drug for internal use.

2. The oral preparation according to claim 1, further comprising water.

3. The oral preparation according to claim 1, further comprising a surfactant.

4. The oral preparation according to claim 1,
wherein
the absorption promotor, together with the soybean oil, form micelles; and
the micelles have an average particle diameter of not more than 1000 nm.

5. The oral preparation according to claim 4, wherein not less than 5% of the micelles each have a particle diameter of not more than 100 nm.

6. The oral preparation according to claim 1, further comprising water, wherein
the absorption promotor is present in an amount of 5% by weight to 20% by weight;
the soybean oil is present in an amount of 5% by weight to 30% by weight; and
the water is present an amount of 50% by weight to 90% by weight.

7. The oral preparation according to claim 1, wherein in the formula (A), n is 1.

* * * * *

UNITED STATES PATENT AND TRADEMARK OFFICE
CERTIFICATE OF CORRECTION

PATENT NO. : 11,219,688 B2
APPLICATION NO. : 16/489181
DATED : January 11, 2022
INVENTOR(S) : Mitsuru Sugawara et al.

Page 1 of 1

It is certified that error appears in the above-identified patent and that said Letters Patent is hereby corrected as shown below:

In the Claims

Column 23, Lines 16-20, delete " 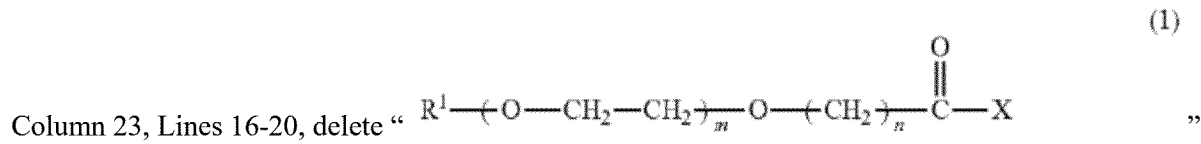 "

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*